(12) United States Patent
Pait et al.

(10) Patent No.: US 12,159,698 B2
(45) Date of Patent: *Dec. 3, 2024

(54) SYSTEM FOR PROVIDING AGGREGATED PATIENT DATA

(71) Applicant: CareFusion 303, Inc., San Diego, CA (US)

(72) Inventors: Clifton Pait, San Diego, CA (US); Ryan Nguyen, San Marcos, CA (US); Vikas Gupta, Naperville, IL (US)

(73) Assignee: CareFusion 303, Inc., San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/543,612

(22) Filed: Dec. 6, 2021

(65) Prior Publication Data

US 2022/0093226 A1   Mar. 24, 2022

Related U.S. Application Data

(63) Continuation of application No. 13/931,282, filed on Jun. 28, 2013, now Pat. No. 11,195,598.

(51) Int. Cl.
    *G16H 10/60* (2018.01)
    *G06Q 10/10* (2023.01)
    *G16Z 99/00* (2019.01)

(52) U.S. Cl.
    CPC ............. *G16H 10/60* (2018.01); *G06Q 10/10* (2013.01); *G16Z 99/00* (2019.02)

(58) Field of Classification Search
    CPC ......... G16H 10/60; G06Q 10/10; G16Z 99/00
    (Continued)

(56) References Cited

U.S. PATENT DOCUMENTS

| 7,904,305 B2 | 3/2011 | Suringa |
| 2002/0007287 A1 | 1/2002 | Straube |

(Continued)

FOREIGN PATENT DOCUMENTS

| KR | 1020100074598 | 7/2010 |
| WO | WO-2000072181 A2 | 11/2002 |

OTHER PUBLICATIONS

United Arab Emirates Office Action for Application No. UAE/P/1726/2015, first received Oct. 10, 2022, 10 pages.

(Continued)

*Primary Examiner* — Karen A Hranek
*Assistant Examiner* — Teresa S Williams
(74) *Attorney, Agent, or Firm* — Morgan, Lewis & Bockius LLP

(57) ABSTRACT

A system for providing aggregated patient data may include a processor and memory. The processor may receive clinical data items from a healthcare data system and device data items from healthcare devices, where the clinical data items and the device data items are associated with patients. The processor may generate patient data objects corresponding to the patients, where each patient data object includes the clinical data items and the device data items associated with one of the patients. The processor may filter the patient data objects based on access privileges of a third party organization to generate filtered patient data objects and transform the filtered patient data objects based on a data transformation rule associated with the third party organization to generate transformed patient data objects. The processor may provide, e.g. over a network, the transformed patient data objects to at least one device associated with the third party organization.

20 Claims, 7 Drawing Sheets

(58) Field of Classification Search
USPC .......................................................... 705/3
See application file for complete search history.

(56) References Cited

U.S. PATENT DOCUMENTS

| | | | |
|---|---|---|---|
| 2002/0128860 A1 | 9/2002 | Leveque et al. | |
| 2003/0014959 A1 | 1/2003 | Ginter | |
| 2003/0149597 A1 | 8/2003 | Zaleski | |
| 2003/0208465 A1 | 11/2003 | Yurko et al. | |
| 2004/0199781 A1 | 10/2004 | Erickson | |
| 2005/0108057 A1* | 5/2005 | Cohen | G16H 40/20 705/3 |
| 2006/0042632 A1 | 3/2006 | Bishop | |
| 2006/0247947 A1 | 11/2006 | Suringa | |
| 2007/0294111 A1* | 12/2007 | Settimi | G16H 10/60 705/3 |
| 2008/0046292 A1 | 2/2008 | Myers et al. | |
| 2008/0091466 A1 | 4/2008 | Butler et al. | |
| 2008/0103828 A1 | 5/2008 | Squilla | |
| 2009/0319295 A1* | 12/2009 | Kass-Hout | G16H 50/80 707/999.102 |
| 2010/0169263 A1 | 7/2010 | Korpman et al. | |
| 2011/0029562 A1 | 2/2011 | Whitby et al. | |
| 2011/0295622 A1 | 12/2011 | Farooq | |
| 2014/0244296 A1* | 8/2014 | Linn | G16H 40/20 705/3 |
| 2015/0328403 A1 | 11/2015 | Dobbles | |

OTHER PUBLICATIONS

Australian Office Action for Application No. 2014302613, dated Apr. 5, 2019, 3 pages.
Australian Office Action for Application No. 2014302613, dated Sep. 16, 2019, 3 pages.
Brazil Office Action for Application No. BR112015032301-4, published Mar. 3, 2020, 4 pages.
Canadian Office Action for Application No. 2916606, dated Feb. 5, 2021, 8 pages.
Canadian Office Action for Application No. 2916606, dated Jul. 3, 2020, 8 pages.
Chinese Office Action for Application No. 201480047904.8, dated Sep. 4, 2019, 27 pages.
European Decision to Refuse European Patent Application for Application No. 14817428.7, dated Apr. 2, 2019, 15 pages.
Extended European Search Report for Application No. 14817428.7, dated Feb. 1, 2017, 11 pages.
Indian Office Action for Application No. 201637000494, dated Oct. 16, 2020, 8 pages.
International Search Report and Written Opinion for International Application No. PCT/US2014/043948, dated Oct. 14, 2014, 8 pages.
Memo concerning Mexican Office Action for Mexican Patent Application No. MX/a/2015/017809, memo mailed Jul. 12, 2018, 3 pages.
Memo concerning Mexican Office Action for Patent Application No. MX/a/2015/017809, memo mailed Jan. 15, 2019, 4 pages.
Memo for Mexican Office Action for Application No. MX/a/2015/017809, memo mailed Jun. 24, 2019, 4 pages.
Summons to attend oral proceedings and communication from the Examining Division for European Application No. 14817428.7, dated Sep. 4, 2018, 12 pages.
United Arab Emirates Office Action from KIPO for Application No. UAE/P/1726/2015, first received Dec. 12, 2019, 10 pages.

* cited by examiner

SYSTEM FOR PROVIDING AGGREGATED PATIENT DATA

CROSS REFERENCE TO RELATED APPLICATIONS

This is a continuation of U.S. application Ser. No. 13/931,282, filed on Jun. 28, 2013, now U.S. Pat. No. 11,195,598, the entirety of which is incorporated herein by reference.

TECHNICAL FIELD

The present description relates generally to patient data, and more particularly, but not exclusively, to providing aggregated patient data.

BACKGROUND

Third party payers, such as insurance companies, are often responsible for the costs associated with a patient's treatment at a healthcare facility, such as a hospital. Although the third party payer may receive an itemized bill for the patient's treatment after a patient has been discharged, the third party payer may have little insight into the patient's treatment as it is occurring. Furthermore, the third party payer may have little insight into the conditions of the healthcare facility where the patient is receiving treatment. Since the third party payer only becomes aware of the patient's treatment after it has completed, e.g. when the third party payer receives a bill for the treatment, the third party payer may be unable to implement programs/interventions while the patient is receiving treatment that may improve the patient's outcome and, consequently, may reduce the costs incurred by the third party payer.

SUMMARY

The disclosed subject matter relates to a method for providing aggregated patient data. The method may include receiving clinical data items from at least one healthcare data system and healthcare device data items from healthcare devices, wherein each of the clinical data items and each of the healthcare device data items are associated with one of a plurality of patients. The method may further include generating a plurality of patient data objects corresponding to the plurality of patients, wherein each of the plurality of patient data objects comprises the clinical data items and the healthcare device data items associated with one of the plurality of patients. The method may further include filtering the plurality of patient data objects based at least in part on access privileges of a third party organization to generate a filtered plurality of patient data objects. The method may further include transforming, by at least one processor, the filtered plurality of patient data objects based at least in part on at least one data transformation rule associated with the third party organization to generate a transformed plurality of patient data objects. The method may further include providing, over a network, the transformed plurality of patient data objects to at least one device associated with the third party organization.

The disclosed subject matter also relates to a system for providing aggregated patient data. The system includes one or more processors and a memory including instructions that, when executed by the one or more processors, cause the one or more processors to: receive clinical data items from at least one healthcare data system and healthcare device data items from healthcare devices, wherein each of the clinical data items and each of the healthcare device data items are associated with one of a plurality of patients, generate a plurality of patient data objects corresponding to the plurality of patients, wherein each of the plurality of patient data objects comprises the clinical data items and the healthcare device data items associated with one of the plurality of patients, filter the plurality of patient data objects based at least in part on access privileges of a third party organization to generate a filtered plurality of patient data objects, augment the filtered plurality of patient data objects using an algorithm that is based at least in part on a condition specific data set to generate an augmented plurality of patient data objects, and transmit, to at least one device associated with the third party organization, a notification that is based at least in part on the augmented plurality of patient data objects.

The disclosed subject matter also relates to a machine-readable medium embodying instructions that, when executed by a machine, allow the machine to perform a method for providing aggregated patient-specific data. The method may include receiving a plurality of data items from at least one healthcare data system and from healthcare devices, wherein each of the plurality of data items is associated with one of a plurality of patients. The method may further include generating a plurality of patient data objects corresponding to the plurality of patients, wherein each of the plurality of patient data objects comprises the data items of the plurality of data items that are associated with the one of the plurality of patients. The method may further include filtering the plurality of patient data objects based at least in part on access privileges of a third party organization to generate a filtered plurality of patient data objects. The method may further include generating trend information based at least in part on the plurality of patient data objects. The method may further include providing, to at least one device associated with the third party organization, a user interface for display that includes at least a portion of the trend information and a filter for filtering the trend information.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF THE DRAWINGS

Certain features of the subject technology are set forth in the appended claims. However, for purpose of explanation, several implementations of the subject technology are set forth in the following figures.

DETAILED DESCRIPTION

Figure 1:
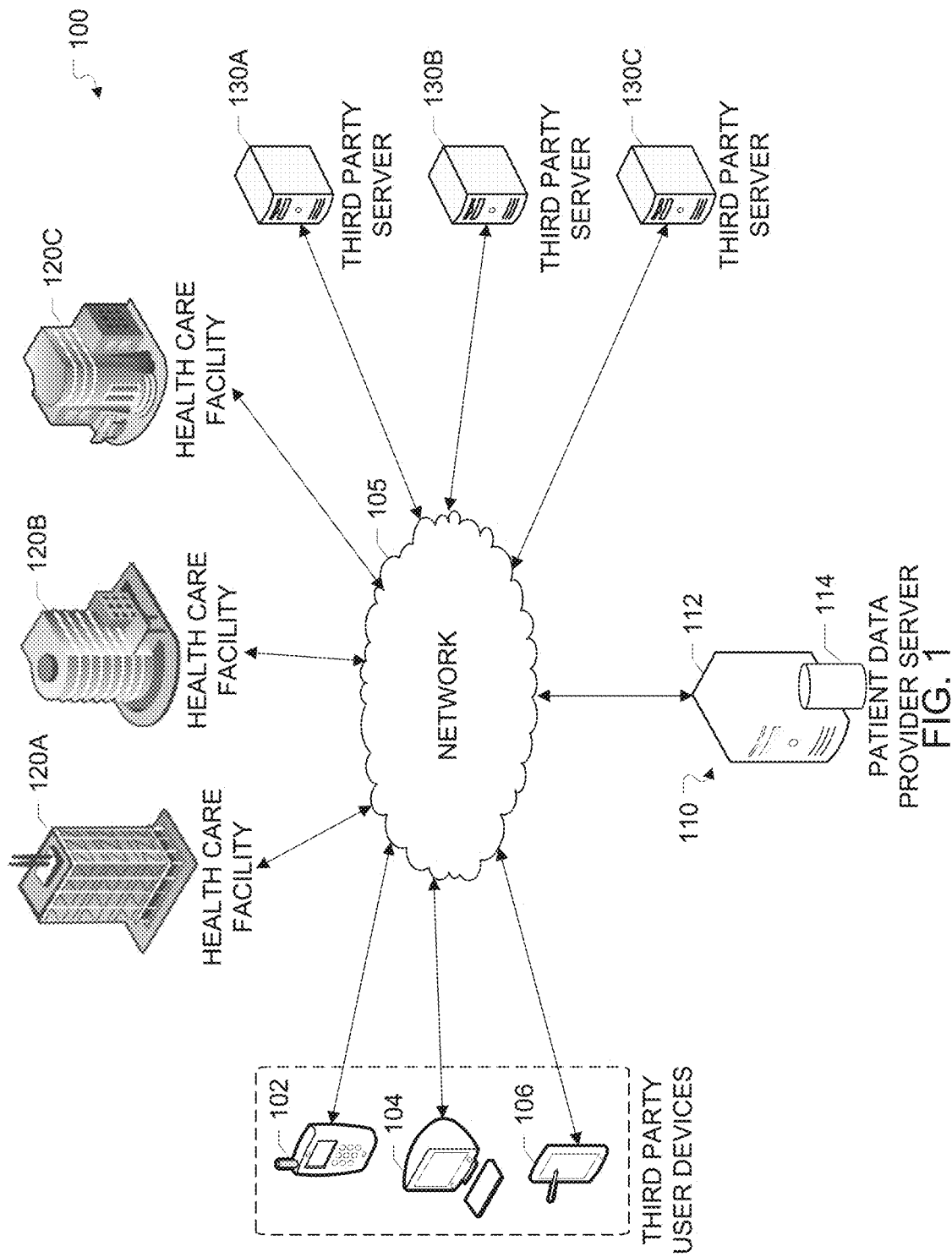
FIG. 1 illustrates an example network environment in which a system for providing aggregated patient data may be implemented in accordance with one or more implementations.

The detailed description set forth below is intended as a description of various configurations of the subject technology and is not intended to represent the only configurations in which the subject technology may be practiced. The appended drawings are incorporated herein and constitute a part of the detailed description. The detailed description includes specific details for the purpose of providing a thorough understanding of the subject technology. However, it will be clear and apparent to those skilled in the art that the subject technology is not limited to the specific details set forth herein and may be practiced using one or more implementations. In one or more instances, well-known structures and components are shown in block diagram form in order to avoid obscuring the concepts of the subject technology.

The subject system provides third party organizations, such as third party payers, with concurrent, transactional-level patient information that is aggregated from one or more healthcare facilities. The patient information may be provided to the third party organizations in a format that allows the third party organization to integrate the patient information into their own systems or other systems. The subject system maps, transforms, and/or normalizes the patient information into data structures that are accessible by the third party organization. The subject system may filter the patient information to only include the information pertaining to patients that the third party organization is authorized to view information for, such as patients for which the third party payer is responsible for healthcare costs.

The subject system also provides third party organizations with visual, graphical information displays of trends and patient specific status that shows concurrent (and retrospective) medical information related to the patients that the third party organization is authorized to view information for. The user interfaces that display the information may be modular within a web browser or an application for desktops, laptops, tablets, mobile phones, or generally any user device. The user interfaces may show information structured specifically for the type of user (of the third party organization) that is viewing the information and the type of clinical case management being performed by the user. In one or more implementations, the subject system may provide authorized healthcare providers of the healthcare facility with views of the information provided to the third party organization.

The subject system may also transmit concurrent, condition specific and patient specific markers and notifications to the authorized users of third party organizations, e.g. over a network and to the users' preferred hardware, such as desktop computers, laptop computers, tablet devices, or mobile phones. The subject system may augment the aggregated patient information using algorithms that are built using condition specific data sets, and may generate the markers and/or notifications by comparing patient medical status and disease state to one or more of desired parameters, care maps, and/or device protocols.

The subject system may also provide third party organizations with user interfaces that include visual, graphical, statistical information displays of patient population trends that can be filtered by patient, by healthcare facility, by region, by state, by condition, or generally by any demographic or treatment grouping. The user interfaces may display retrospective medical information, for patients that the third party organization is authorized to view, from the acute care setting and the outpatient setting regardless of the healthcare facility. The trends may also be filtered based on time periods, such as daily, weekly, monthly, quarterly, annually, or generally any time period. The information displayed in the user interfaces may be tailored to the type of user and the type of healthcare facility performance being tracked.

FIG. 1 illustrates an example network environment 100 in which a system for providing aggregated patient data may be implemented in accordance with one or more implementations. Not all of the depicted components may be required, however, and one or more implementations may include additional components not shown in the figure. Variations in the arrangement and type of the components may be made without departing from the spirit or scope of the claims as set forth herein. Additional, different or fewer components may be provided.

The example network environment 100 includes a network 105, healthcare facilities 120A-C, a patient data provider server 110, third party servers 130A-C, and third party user devices 102, 104, 106. The healthcare facilities 120A-C may represent hospitals, groups of hospitals, urgent care centers, integrated delivery networks (IDNs), or generally any location where patient data may be generated. The healthcare facilities 120A-C may each include one or more interconnected computing devices and/or healthcare devices, at least one of which is communicatively coupled to the network 105. An example healthcare facility 120A is discussed further below with respect to FIG. 2. The third party servers 130A-C may each be associated with different third party organizations, such as payer organizations, insurance companies, government agencies, employers, group purchasing organizations (GPOs), or generally any third party organization. Similarly, the third party user devices 102, 104, 106 may be accessed by users that are associated with one of the aforementioned third party organizations.

The at least one computing device of each of the healthcare facilities 120A-C, the patient data provider server 110, the third party servers 130A-C, and third party user devices 102, 104, 106 may be communicatively coupled to one another, such as by the network 105. The patient data provider server 110, the third party servers 130A-C, and the third party user devices 102, 104, 106 may be, or may include all or part of, the electronic system that is discussed below with respect to FIG. 7. The network 105 may be a communication network, such as a public communication network (such as the Internet, cellular data network, dialup modems over a telephone network), a private communications network (such as private local area network ("LAN"), leased lines), etc. The network 105 may also include, but is not limited to, any one or more of the following network topologies, including a bus network, a star network, a ring network, a mesh network, a star-bus network, a tree or hierarchical network, and the like. The connections of the network 105 may be wired or wireless.

The patient data provider server 110 and/or one or more of the third party servers 130A-C may each be a single computing device such as a computer server. In another example, the patient data provider server 110 and/or one or more of the third party servers 130A-C may each represent one or more computing devices (such as a cloud of computers and/or a distributed system) that are communicatively coupled, such as communicatively coupled over the network 105, that collectively, or individually, perform one or more functions that can be performed server-side. The one or more computing devices of the patient data provider server 110 and/or the third party servers 130A-C may each be geographically collocated or disparately located. The patient data provider server 110 and/or the third party servers 130A-C may each be coupled with various databases, storage services, or other computing devices. The patient data provider server 110 and/or the third party servers 130A-C, and the coupled databases, storage services, or other computing devices may each be geographically collocated, or may be disparately located.

In one or more implementations, the patient data provider server 110 includes a processing device 112 and a data store 114. The processing device 112 executes computer instructions stored in the data store 114, for example, to provide aggregated patient data. In one or more implementations, the data store 114 may store the computer instructions on non-transitory computer-readable medium.

In some example implementations, the third party user devices 102, 104 and 106 can be computing devices such as laptop or desktop computers, smartphones, personal digital assistants ("PDAs"), portable media players, tablet computers, wearable devices, such as eyeglasses or watches that have one or more processors coupled thereto and/or embedded therein, televisions or other displays with one or more processors coupled thereto and/or embedded therein, or other appropriate computing devices that can be used to for displaying a web page, a web application, a mobile application, or another graphical user interface. In the example of FIG. 1, the third party user device 102 is depicted as a smartphone, the third party user device 104 is depicted as a desktop computer, and the third party user device 106 is depicted as a tablet device.

In operation, the patient data provider server 110 may receive patient information from each of the healthcare facilities 120A-C over the network 105. The patient information may include both clinical/laboratory information for patients and information generated by healthcare devices associated with the patients, such as infusion devices, ventilator devices, automated dispensing machines (ADMs), etc. The patient data provider server 110 aggregates the patient information and provides the patient information, in various forms, to any of the third party servers 130A-C and/or any of the third party user devices 102, 104, 106. For example, the patient data provider server 110 may transform the patient information based on one or more data transformation rules received from a third party organization. The patient data provider server 110 may provide the transformed patient information to a third party server 130A that is associated with the third party organization. An example process for providing transformed patient information to a third party server 130A is discussed further below with respect to FIG. 3. Alternatively, or in addition, the patient data provider server 110 may provide condition specific and/or patient specific markers and/or notifications to one or more of the third party user devices 102, 104, 106. An example process for providing markers and/or notifications to a third party user device 102 is discussed further below with respect to FIG. 4.

Figure 2:
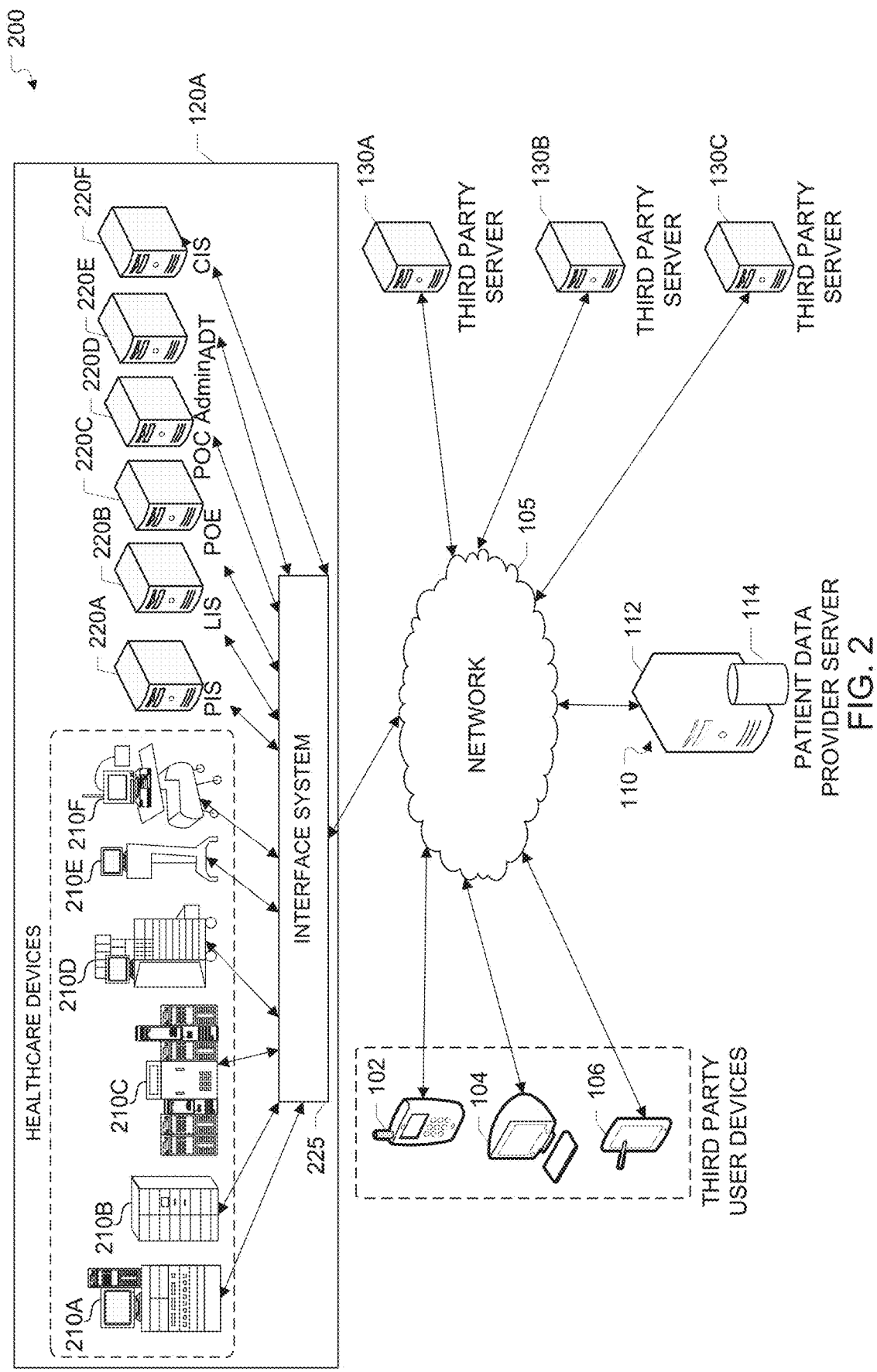
FIG. 2 illustrates an example network environment in which a system for providing aggregated patient data may be implemented in accordance with one or more implementations.

FIG. 2 illustrates an example network environment 200 in which a system for providing aggregated patient data may be implemented in accordance with one or more implementations. Not all of the depicted components may be required, however, and one or more implementations may include additional components not shown in the figure. Variations in the arrangement and type of the components may be made without departing from the spirit or scope of the claims as set forth herein. Additional, different or fewer components may be provided.

The example network environment 200 includes a network 105, a healthcare facility 120A, a patient data provider server 110, third party servers 130A-C, and third party user devices 102, 104, 106. The healthcare facility 120A includes one or more healthcare devices 210A-F, healthcare data systems 220A-F, and an interface system 225. The healthcare data systems 220A-F may include a pharmacy information system (PIS) 220A, a laboratory information system (LIS) 220B, a physician order entry (POE) system 220C, a point of care (POC) admin system 220D, an admit-discharge-transfer (ADT) system 220E, and a clinical information system (CIS) 220F. The interface system 225 may communicatively couple the healthcare devices 210A-F and/or one or more of the healthcare data systems 220A-F with the network 105. Alternatively, or in addition, one or more of the healthcare devices 210A-F and/or one or more of the healthcare data systems 220A-F may be coupled directly to the network 105, e.g. without communicating through the interface system 225. The interface system 225, the patient data provider server 110, third party servers 130A-C, and third party user devices 102, 104, 106 may be communicatively coupled to one another, such as by the network 105. In one or more implementations, one or more of the healthcare data systems 220A-F may be hosted within the healthcare facility 120A and/or one or more of the healthcare data systems 220A-F may be hosted externally to the healthcare facility 120A.

The interface system 225 and/or one or more of the healthcare data systems 220A-F may each be a single computing device such as a computer server. In another example, the interface system 225 and/or one or more of the healthcare data systems 220A-F may each represent one or more computing devices (such as a cloud of computers and/or a distributed system) that are communicatively coupled, such as communicatively coupled over the network 105, that collectively, or individually, perform one or more functions that can be performed server-side. The one or more computing devices of the interface system 225 and/or one or more of the healthcare data systems 220A-F may each be geographically collocated or disparately located. The interface system 225 and/or one or more of the healthcare data systems 220A-F may each be coupled with various databases, storage services, or other computing devices. The interface system 225 and/or one or more of the healthcare data systems 220A-F, and the coupled databases, storage services, or other computing devices may each be geographically collocated, or may be disparately located. In one or more implementations, the interface system 225 and/or one or more of the healthcare data systems 220A-F may each be, or may each include all or part of, the electronic system that is discussed below with respect to FIG. 7.

The healthcare devices 210A-F may be any device that provides healthcare to a patient, or facilitates providing healthcare to a patient. The healthcare devices 210A-F may include infusion devices, such as infusion pumps, drug delivery devices, dispensing devices, such as automated dispensing machines, monitoring devices, respiratory devices, such as ventilators, waste devices, such as drug disposal devices, or generally any device that may facilitate with providing healthcare to patients and/or may provide healthcare to patients. In one or more implementations, the monitoring devices may include blood pressure monitoring devices, devices for monitoring during sedation, or devices that monitor a patient's vital signs and/or a patient's physiological response. One or more of the healthcare devices 210A-F may include a processor and/or a memory. Alternatively, or in addition, one or more of the healthcare devices 210A-F may be communicatively coupled to a device that includes a processor and a memory, such as via a serial port. In one or more implementations, one or more of the healthcare devices 210A-F may be, or may include all or part of, the electronic system that is discussed below with respect to FIG. 7.

For example, the healthcare devices 210A-F may include automated dispensing machines (ADM), such as Pyxis Medstations™, which store and dispense medications at nurse's stations, thereby providing distributed access to medications. The healthcare devices 210A-F may further include infusion devices, such as infusion pumps, that assist with administering medications to patients. The healthcare devices 210A-F may also include waste devices that accept and store wasted medications, e.g. excess medications, from healthcare professionals and track the amount of medications wasted by healthcare professionals.

In one or more implementations, the PIS 220A may store, for example, information pertaining to a pharmacy of a healthcare facility, such as outstanding orders, filled orders, patient medical profiles/histories, etc. For example, the PIS 220A may provide a library of drug allergies and adverse drug interactions against which each incoming order, or prescription, is checked as part of the order entering/drug dispensing process to identify possible allergies and adverse drug interactions and help in preventing administration of drugs to a patient where the patient might be injured by the prescribed course of therapy. Additionally, the PIS 220A may check to determine if any therapies are being duplicated, such as where two or more drugs might be used to treat a diagnosed disease, whether they are synergistic or antagonistic, and whether the prescribed therapy should be modified accordingly.

In one or more implementations, LIS 220B may store lab results and/or other clinical information for patients receiving healthcare through the healthcare facility 120A. The POE system 220C may be used, for example, by physicians to enter orders for patients, such as orders for medications to be administered to patients, that are then transmitted to the PIS 220A. The POC admin system 220D may include any point of contact information besides administration and documentation applications. The ADT system 220E may store, for example, patient administration information, such as information regarding patient admit, discharge, transfer, registration, etc. The CIS 220F may store any other clinical information for patients receiving healthcare through the healthcare facility 120A, e.g. any information that is not stored in one of the healthcare data systems 220A-F. In one or more implementations, the CIS 220F may include one or more of the other healthcare data systems 220A-F.

In one or more implementations, the interface system 225 receives messages, e.g. containing data and/or information, in a first external format, e.g. a format native to the healthcare devices 210A-F and/or the healthcare data systems 220A-F, converts the messages into an internal messaging format, e.g. for processing and storing the messages, and converts the messages into a second external format, e.g. a format native to the patient data provider server 110, and then transmits the messages in the second external format to the patient data provider server 110. In one or more implementations, the first external format may be the same as the second external format. In one or more implementations, the interface system 225 may be, and/or may include all or part of, a coordination engine. At least a portion of the interface system 225 may be implemented as described, for example, in U.S. patent application Ser. No. 13/421,776, entitled "Scalable Communication System," filed on Mar. 15, 2012, which has been incorporated by reference in its entirety for all purposes.

The interface system 225 includes an adapter, i.e. an interface module, for each external device or data system that is part of the hospital's data system. In certain embodiments, an adapter can have more than one interface module. Each adapter is built from a common basic structure, or "framework", and customized according to the particular native message format used by the external device to be connected to that adapter. The interface system 225 also includes a core that transfers messages in an internal messaging format between the adapters. The internal messaging format is common to all internal messaging format messages regardless of which adapter is providing the internal messaging format message or which adapter is receiving the internal messaging format message.

Data in different formats from the external data systems are mapped and/or transformed into a common messaging system (CMS) format, also referred to herein as an "internal messaging format." Once data from a sending external data system is provided by an adapter in the internal messaging format, this data can be changed (or "converted" or "mapped" or "translated", "transformed", etc.) by the interface system 225, for example, into any of the other formats of the receiving (or "destination" or "target") data systems according to certain aspects of the present disclosure. Hence, the sending data systems and the receiving data systems are still able to operate according to their own native data format and protocols, with the interface system 225 performing the translation to allow a sending data system to communicate with a receiving data system.

The interface system 225 provides a modular, extendible, and scalable communication system that can exchange information between any information systems or networked devices. Information from a single sending device or system can be selectively broadcast to predetermined destination devices and systems rather than broadcast to every device on the network. Information may be filtered and processed at one or more selectable points in the communication flow between systems. In certain embodiments, incoming messages are received in their native message format and protocol and converted to an internal messaging format for internal handling in the interface system 225, then converted to the native message format of a receiving system and sent to that system per its native protocol.

In operation, the healthcare devices 210A-F may generate healthcare device data that relates to the healthcare being provided by, or facilitated by, the healthcare devices 210A-F. The healthcare device data may include, e.g., data pertaining to the healthcare being provided, or facilitated, by the healthcare devices 210A-F and/or settings of the healthcare devices 210A-F. The healthcare devices 210A-F may transmit the healthcare device data to the interface system 225.

The interface system 225 may provide the healthcare device data to one or more hospital systems, and may provide the healthcare device data to the patient data provider server 110.

One or more of the healthcare data systems 220A-F may receive patient clinical data, such as lab results, diagnostic data, radiology data, or generally any clinical data, and may provide the patient clinical data to the patient data provider server 110 and to one or more hospital systems. The patient data provider server 110 may receive the healthcare device data from the healthcare devices 210A-F and the patient clinical data from one or more of the healthcare data systems 220A-F. The patient data provider server 110 may aggregate the received healthcare device data and clinical data, e.g. on a per patient basis, may transform the aggregated data based on one or more rules, and may provide the transformed data to one or more of the third party servers 130A-C and/or the third party user devices 102, 104, 106.

Figure 3:
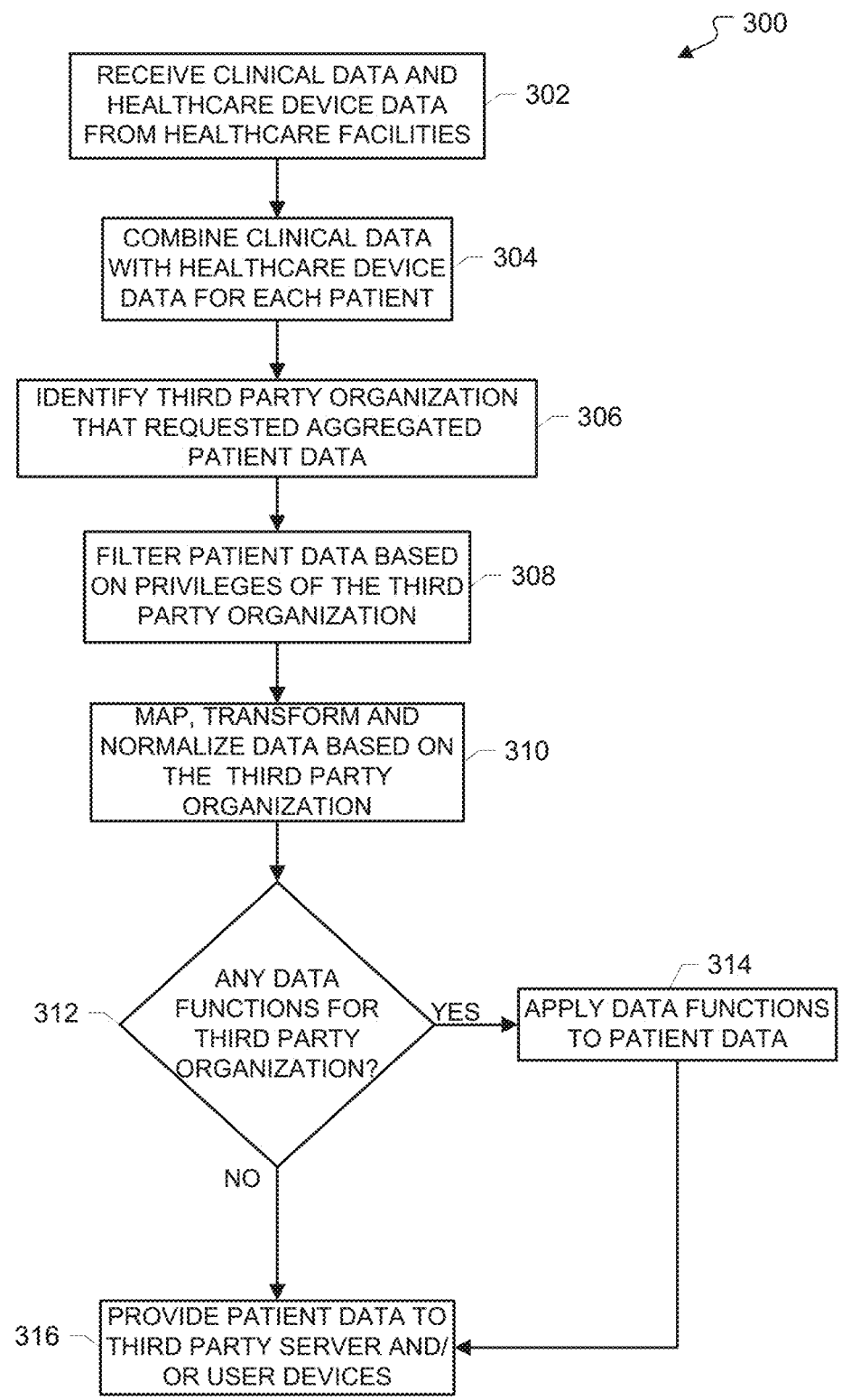
FIG. 3 illustrates a flow diagram of an example process for a system for providing aggregated patient data in accordance with one or more implementations.

FIG. 3 illustrates a flow diagram of an example process 300 for a system for providing aggregated patient data in accordance with one or more implementations. For explanatory purposes, the example process 300 is described herein with reference to the patient data provider server 110 of the example network environments 100, 200 of FIGS. 1 and 2; however, the example process 300 is not limited to the patient data provider server 110 the example network environments 100, 200 of FIGS. 1 and 2. For example, one or more blocks of the example process 300 may be performed by another server. Further for explanatory purposes, the blocks of the example process 300 are described herein as occurring in serial fashion, or linearly. However, multiple blocks of the example process 300 may occur in parallel. In addition, the blocks of the example process 300 need not be performed in the order shown and/or one or more of the blocks of the example process 300 need not be performed.

In block 302, the patient data provider server 110 receives clinical data and healthcare device data from the healthcare facilities 120A-C over the network 105. For example, the healthcare facilities 120A-C may each include an interface system 225 that transmits clinical data, e.g. from one or more of the healthcare data systems 220A-F and healthcare device data, e.g. from the healthcare devices 210A-F, to the patient data provider server 110. In block 304, the patient data provider server 110 combines the clinical data with the healthcare device data for each patient to generate patient data objects. For example, the patient data provider server 110 may determine the clinical data and healthcare device data that is associated with a given patient and the patient data provider server 110 may aggregate the data associated with the given patient into a patient data object. Thus, there may be one patient data object for each patient, and the patient data object for a patient may include information that identifies the patient, such as the patient's name, as well as information that identifies a third party payer associated with the patient, such as a third party payer identifier. For example, the patient data provider server 110 may receive billing information from the healthcare facilities 120A-C, and the patient data provider server 110 may determine a third party payer associated with the billing information for each patient.

In block 306, the patient data provider server 110 identifies a third party organization that has requested aggregated patient data. For example, the patient data provider server 110 may receive requests from one or more third party organizations, e.g. via the third party servers 130A-C, for aggregated patient data. The requests may include one or more information items, such as a list of patients for which the third party organization is authorized to access patient data, data mapping rules, data normalization rules, data transformation rules, data functions, or generally any information regarding the requested aggregated patient data and/or the form in which the third party organization would like to receive the requested aggregated patient data.

In block 308, the patient data provider server 110 filters the patient data objects based at least in part on the access privileges of the requesting third party organization. For example, the third party organization may provide a list of the patients for which the third party organization is authorized to access patient information. Alternatively, or in addition, the patient data objects may be associated with an identifier of a third party organization, such as third party payer identifier. Thus, in one or more implementations the patient data provider server 110 may filter the patient data objects based at least in part on an identifier of the third party organization and a third party payer identifier associated with the patient data objects.

In one or more implementations, if the third party organization is not authorized to view the patient data objects that include patient-identifiable data, such as patient names, etc., the patient data provider server 110 may filter the patient data objects by removing any patient-identifiable data from the patient data objects. For example, the patient data provider server 110 may anonymize the patient data objects by replacing patient-identifiable data with patient-unidentifiable data and/or by removing any patient-identifiable data from the patient data objects.

In block 310, the patient data provider server 110 may map, transform, and/or normalize the filtered patient data objects based at least in part on the requesting third party organization. For example, the requesting third party organization may provide the patient data provider server 110 with one or more data mapping rules, data transformation rules, and/or data normalization rules, and the patient data provider server 110 may utilize any received rules to map, transform, and/or normalize the patient data objects. For example, a data mapping rule may be used to map the data fields of the patient data object to data fields utilized by the third party organization, a data transformation rule may be used to transform the patient data object into a data format used by the third party organization, and a data normalization rule may be used to normalize the data values of the patient data objects. For example, a data normalization rule may be used to convert any values of "M" for a gender data field to "male".

In block 312, the patient data provider server 110 determines whether any data functions exist for the third party organization and/or individual users of the third party organization. For example, a third party organization may provide data functions that the third party organization would like applied to the transformed patient data objects. If, in block 312, the patient data provider server 110 determines that at least one data function exists for the requesting third party organization, the patient data provider server 110 moves to block 314. In block 314, the patient data provider server 110 applies the at least one data function to the transformed patient data objects. In one or more implementations, the patient data provider server 110 may provide a graphical user interface to the third party organizations, e.g. via one or more the third party user devices 102, 104, 106, that allows the third party organizations to create and/or manage data mapping rules, data transformation rules, data normalization rules, and/or data functions.

In one or more implementations, data functions may be used to process the patient data objects to provide the third party organizations with additional insight into the patients and/or the healthcare facilities 120A-C. For example, a data function applied to the patient data objects may be used to identify potential outbreaks, and/or specific patients, to better perform programs for outpatient/home infection prevention, which may prevent the spread of illnesses to other family members that are covered by the third party organization. Similarly, a data function may be used to identify patients that missed a clinic infusion visit, multi-drug resistant organisms (MRDO), e.g. integrated culture data, resistant patterns, pathogens specific to identify patients of interest, and caterers/devices pulled from cabinets to identify those at high risk for infection.

Alternatively, or in addition, one or more data functions applied to the patient data objects may also be used to identify ventilated patients in a timely manner that have specific events that may increase their risk for poor outcomes post discharge, e.g. so that programs/intervention can be implemented to improve related outcomes. For example, a data function may process the patient data objects to identify how long patients have been on ventilators, which patients are at risk for going on a ventilator, and/or infection related markers or other information.

Alternatively, or in addition, one or more data functions applied to the patient data objects may also be used to identify patients that are on prolonged sedation or other related medications that may place the patient at risk for poor post discharge outcomes, e.g. so that programs/interventions can be implemented to improve related outcomes. For example, a data function may determine infusion related metrics, such as sedation metrics, Guardrails-harm index metrics, etc.

Alternatively, or in addition, one or more data functions may be applied to the patient data to identify patients that are admitted to the hospital with an anticoagulation safety or other clinical scenario, laboratory abnormality or medication related event, or patients that develop one while in the hospital, so that programs/interventions can be implemented to improve outcomes. For example, such patients may be identified from infusion related metrics, dispensing related metrics (e.g. antidotes for adverse drug events (ADE)), clinical alerts and related metrics, and/or patients entering the emergency department with ADEs, lab abnormalities, the drugs that are given on the day of admission, failure to receive lab values, etc. Some condition specific examples may include, e.g., glycemic control/blood sugar management, heart failure, chronic obstructive pulmonary disease (COPD), acute myocardial infarction, cancer, etc.

Alternatively, or in addition, one or more data functions may be applied to the patient data to track patient populations by healthcare facilities 120A-C (or other population sets), so that related costs, outcomes, and payment strategies can be monitored and/or implemented. Other types of tracking may include, e.g. number of transitions from acute care to ambulatory care or managed in the ambulatory setting, identifying patients that can be managed more efficiently (ambulatory environment), number of wounds or other types of infections that are treated in the acute care setting (e.g. prolonged antibiotic infusion) vs. ambulatory setting, strategies to prevent antimicrobial resistance (appropriate antimicrobial prescribing/administration), aggregate protocol, guideline metrics & protocol, guideline outcomes, benchmarking medical device information, present information as a score card to compare care settings and effectiveness, tracking compliance to the user of medical device safety software, patient-controlled analgesia (PCA) in use with $EtCO_2$, decreases in healthcare-associated and/or hospital-associated infection rates, number of ventilator acquired complications occurring per vent days, sedation holiday episodes, hospitals that are performing better with sedation metrics, a hospital within an integrated delivery network (IDN) that is outperforming other hospitals in the IDN, outpatient infusion therapy, preference card management, COPD, oncology protocols and compliance, and/or retrospective adjustment of metrics by appropriate clinical adjustment.

If, in block 312, the patient data provider server 110 determines that there are no data functions to be applied for the requesting third party organization, the patient data provider server 110 moves to block 316. In block 316, the patient data provider server 110 provides the patient data objects, over the network 105, to the third party server 130A that is associated with the third party organization, and/or to one or more of the third party user devices 102, 104, 106 that are associated with the third party organization. An example data flow for providing the patient data objects to a third party server 130A that is associated with the third party organization is discussed further below with respect to FIG. 5. An example data flow for providing the patient data objects to one or more third party user devices 102, 104, 106 is discussed further below with respect to FIG. 6. In one or more implementations, the blocks 302-316 of FIG. 3 may be repeated for each third party organization that has requested patient data from the patient data provider server 110.

Figure 4:
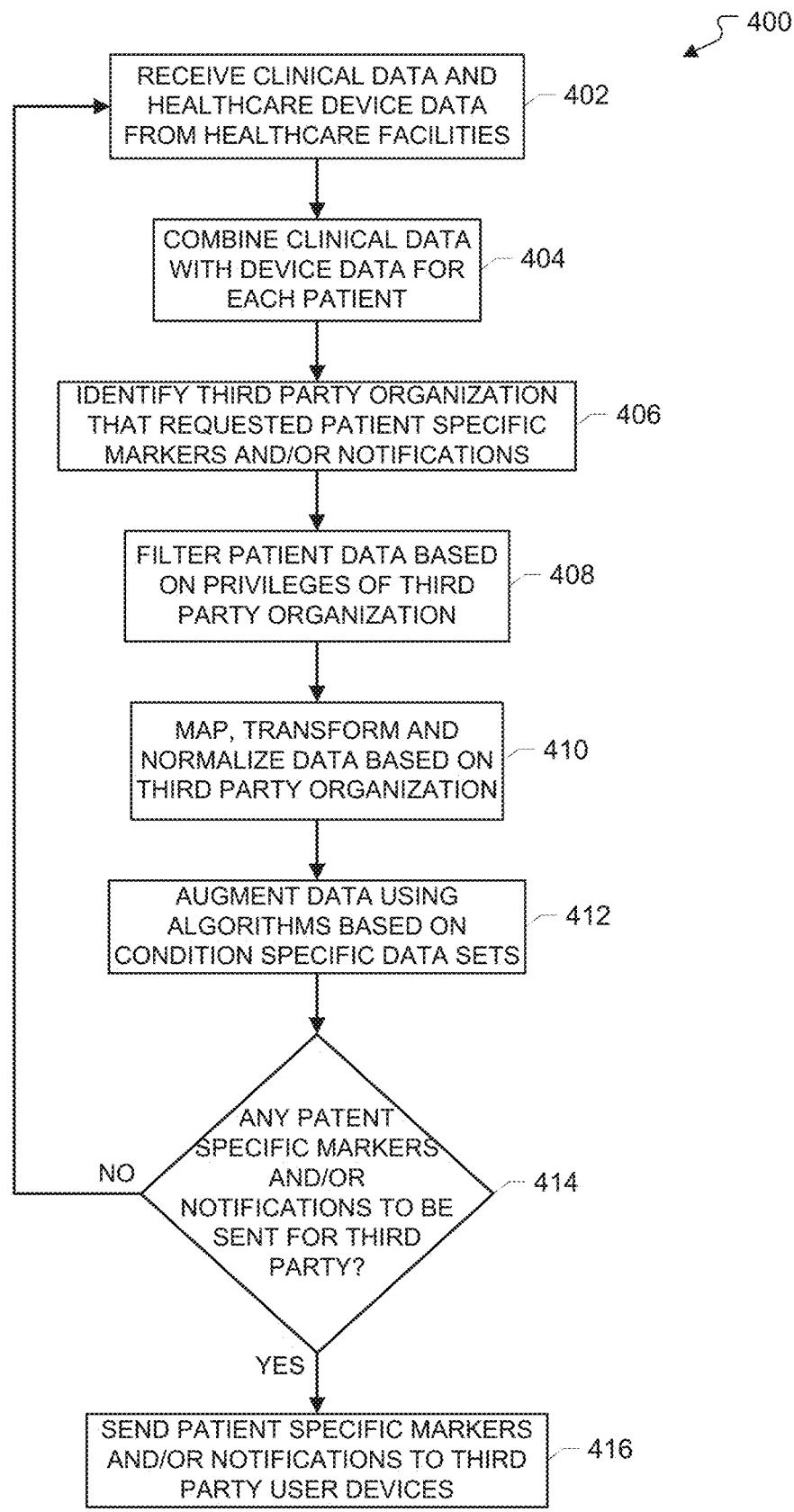
FIG. 4 illustrates a flow diagram of an example process for a system for providing aggregated patient data in accordance with one or more implementations.

FIG. 4 illustrates a flow diagram of an example process 400 for a system for providing aggregated patient data in accordance with one or more implementations. For explanatory purposes, the example process 400 is described herein with reference to the patient data provider server 110 of the example network environments 100, 200 of FIGS. 1 and 2; however, the example process 400 is not limited to the patient data provider server 110 the example network environments 100, 200 of FIGS. 1 and 2. For example, one or more blocks of the example process 400 may be performed by another server. Further for explanatory purposes, the blocks of the example process 400 are described herein as occurring in serial fashion, or linearly. However, multiple blocks of the example process 400 may occur in parallel. In addition, the blocks of the example process 400 need not be performed in the order shown and/or one or more of the blocks of the example process 400 need not be performed.

In block 402, the patient data provider server 110 receives clinical data and healthcare device data from the healthcare facilities 120A-C over the network 105. In block 404, the patient data provider server 110 combines the clinical data with the healthcare device data for each patient to generate patient data objects. In block 406, the patient data provider server 110 identifies a third party organization that has requested patient specific markers and/or notifications. For example, the patient data provider server 110 may receive requests from one or more third party organizations, e.g. via the third party servers 130A-C, for patient specific markers and/or notifications, e.g. when a provided threshold is satisfied by the patient data objects.

In block 408, the patient data provider server 110 filters the patient data objects based at least in part on the access privileges of the requesting third party organization. In block 410, the patient data provider server 110 may map, transform, and/or normalize the filtered patient data objects based at least in part on the requesting third party organization. In block 412, the patient data provider server 110 augments the patient data objects using one or more algorithms based on condition specific data sets. In one or more implementations, the augmenting in block 412 may be skipped.

In block 414, the patient data provider server 110 determines whether any patient specific markers and/or notifications should be sent for the third party organization. For example, the patient data provider server 110 may compare values retrieved from the patient data objects to one or more patient specific marker thresholds. If the any of the values satisfy the patient specific marker thresholds, the patient data provider server 110 may determine that a patient specific marker and/or notification should be sent for the third party organization.

In one or more implementations, the patient data provider server 110 may provide a graphical user interface to the third party organizations, e.g. via one or more the third party user devices 102, 104, 106, that allows the third party organizations to create and/or manage thresholds that pertain to patient specific markers and/or notifications. The user interface may also allow the third party organization to configure the notifications, e.g. the recipients of the notifications, the format of the notifications, etc.

If, in block 414, the patient data provider server 110 determines that there are no patient specific markers and/or notifications to be sent for the third party organization, the patient data provider server 110 returns to block 402 and repeats the example process 400. If, in block 414, the patient data provider server 110 determines that there is at least one patient specific marker and/or notification to be sent for the third party organization, the patient data provider server 110 moves to block 416. In block 416, the patient data provider server 110 transmits the at least one patient specific marker and/or notification, e.g. to one or more of the third party user devices 102, 104, 106 that are associated with the third party organization. The markers and/or notifications may be sent via a message, such as an email, a text message, an instant message, etc., and/or may be sent as part of a user interface provided to the third party user devices 102, 104, 106, such as via a popup window, a dialog box, etc. In one or more implementations, the blocks 402-416 of FIG. 4 may be repeated for each third party organization that has requested patient specific markers and/or notifications from the patient data provider server 110.

Figure 5:
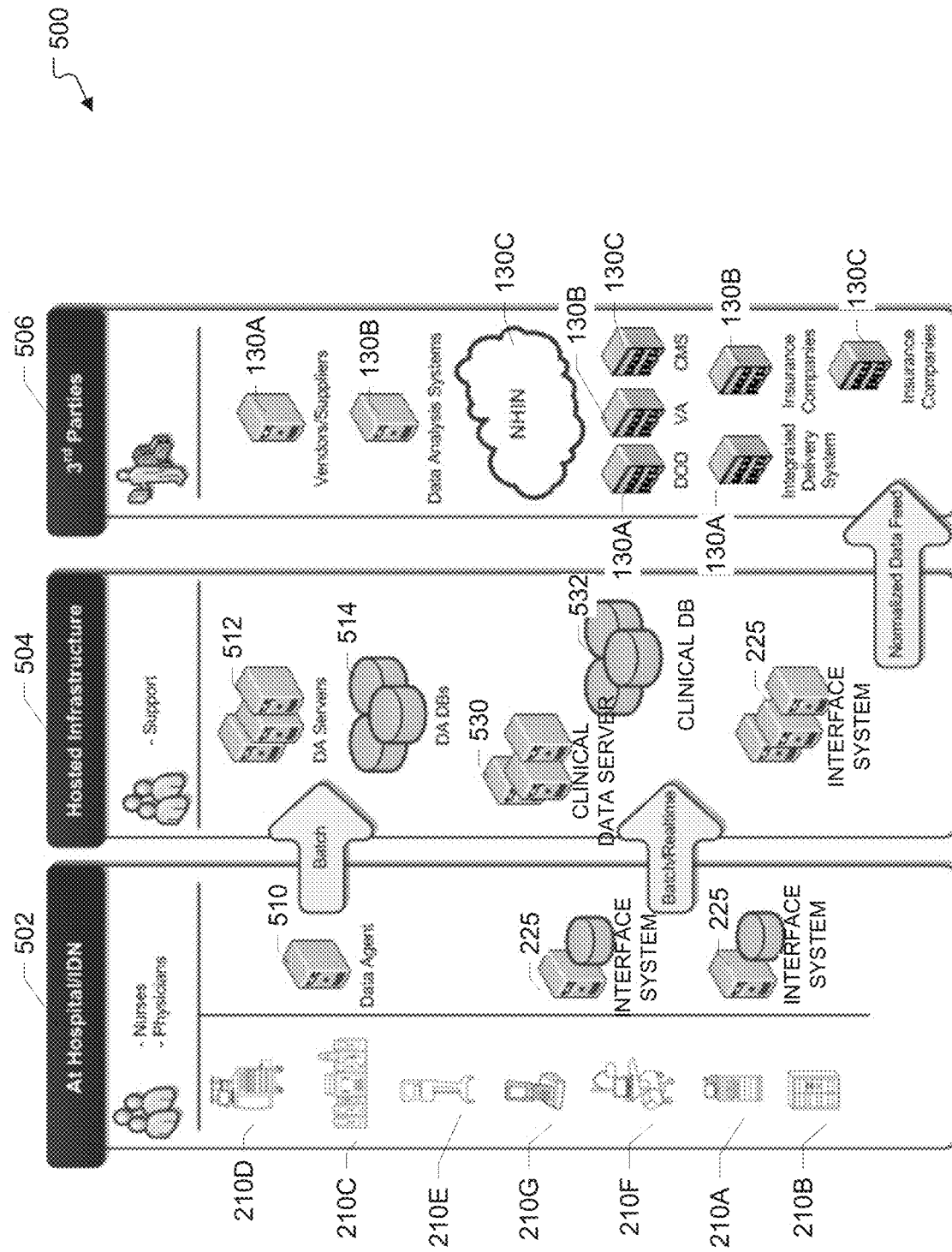
FIG. 5 illustrates an example data flow in a system for providing aggregated patient data in accordance with one or more implementations.

FIG. 5 illustrates an example data flow 500 in a system for providing aggregated patient data in accordance with one or more implementations. Not all of the depicted components may be required, however, and one or more implementations may include additional components not shown in the figure. Variations in the arrangement and type of the components may be made without departing from the spirit or scope of the claims as set forth herein. Additional, different or fewer components may be provided.

The data flow 500 includes a hospital/IDN data flow 502, a hosted infrastructure data flow 504, and a third party data flow 506. In the hospital/IDN data flow 502, healthcare device data is transmitted by the healthcare devices 210A-G to the data agent 510 and/or to the interface system 225. The data agent 510 transmits, in batch form, the healthcare device data to the data agent servers 512 and/or the data agent databases 514 of the hosted infrastructure data flow 504. The interface system 225 transmits the healthcare device data to the interface system 225 of the hosted infrastructure data flow 504 in batch form and/or in real-time.

In the hosted infrastructure data flow 504, the data agent servers 512 and/or data agent databases 514 provide the received healthcare device data to the interface system 225. Similarly, the clinical data server 530 and/or the clinical database 532 provide the clinical and/or lab data to the interface system 225. In one or more implementations, the clinical data server 530 and/or the clinical database 532 may be located within the hospital/IDN data flow 502. The interface system 225 combines the healthcare device data and the clinical data to generate aggregated patient data, and provides a normalized data feed, e.g. the aggregated patient data, to one or more third party systems 130A-C of the third party data flow 506.

Figure 6:
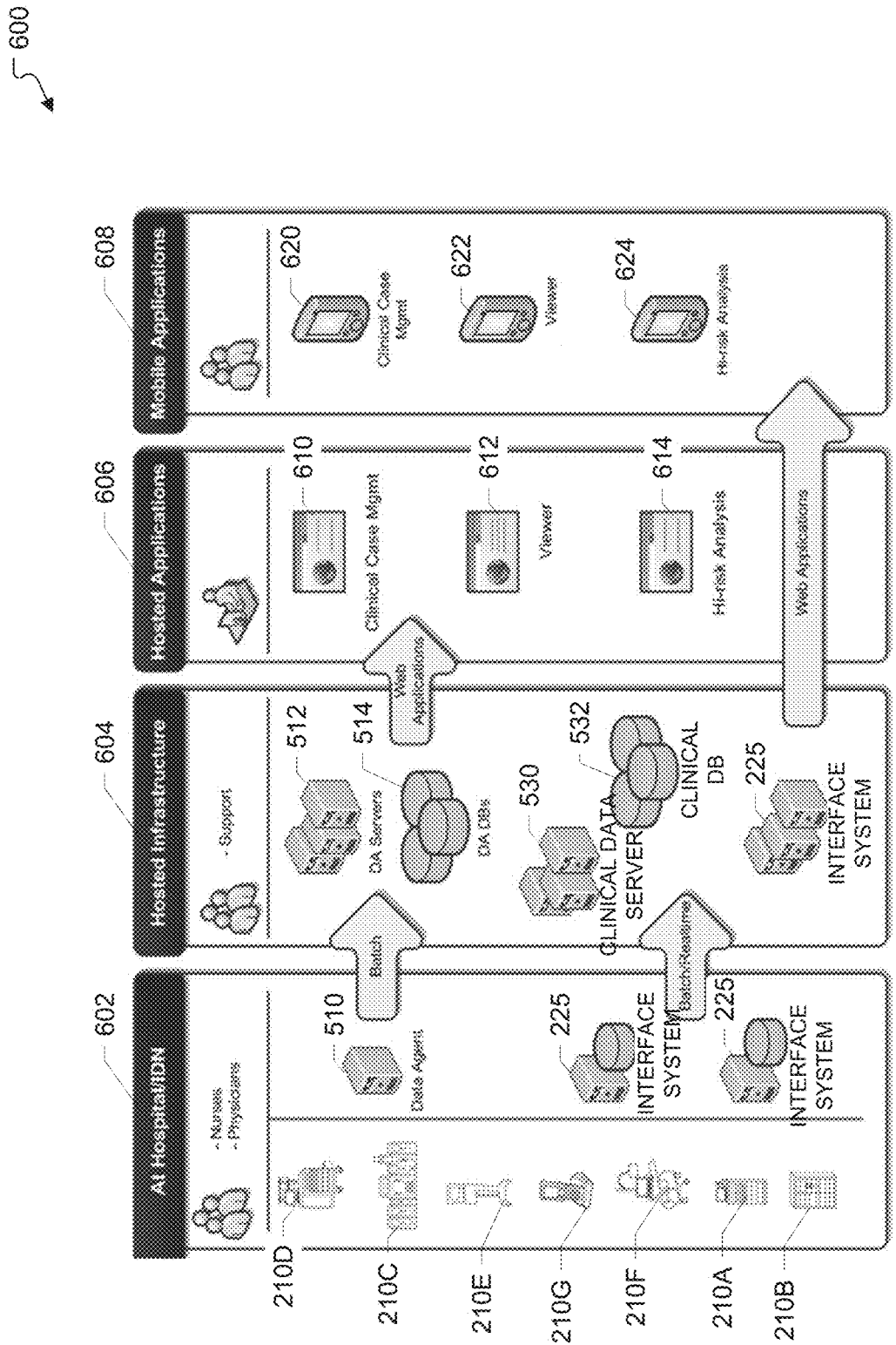
FIG. 6 illustrates an example data flow in a system for providing aggregated patient data in accordance with one or more implementations.

FIG. 6 illustrates an example data flow 600 in a system for providing aggregated patient data in accordance with one or more implementations. Not all of the depicted components may be required, however, and one or more implementations may include additional components not shown in the figure. Variations in the arrangement and type of the components may be made without departing from the spirit or scope of the claims as set forth herein. Additional, different or fewer components may be provided.

The data flow 600 includes a hospital/IDN data flow 602, a hosted infrastructure data flow 604, and a hosted applications data flow 606, and a mobile applications data flow 608. In the hospital/IDN data flow 602, healthcare device data is transmitted by the healthcare devices 210A-G to the data agent 510 and/or to the interface system 225. The data agent 510 transmits, in batch form, the healthcare device data to the data agent servers 512 and/or the data agent databases 514 of the hosted infrastructure data flow 604. The interface system 225 transmits the healthcare device data to the interface system 225 of the hosted infrastructure data flow 604 in batch form and/or in real-time.

In the hosted infrastructure data flow 604, the data agent servers 512 and/or data agent databases 514 receive clinical and/or lab data from the clinical data server 530 and/or the clinical databases 532. The data agent servers 512 combine the healthcare device data with the clinical data to generate aggregated patient data, and provide the aggregated patient data, via web applications, to the hosted applications data flow 606. The clinical data servers 530 and/or the clinical database 532 provide the clinical and/or lab data to the interface system 225. The interface system 225 combines the healthcare device data with the clinical data to generate aggregated patient data and provides the aggregated patient data, via web applications, to the mobile applications data flow 608.

In the hosted applications data flow 606, at least a portion of the aggregated patient data is displayed via a clinical case management tool 610, a viewer 612, and/or a hi-risk analysis tool 614, e.g. on the third party user devices 102, 104, 106. In the mobile applications data flow 608, at least a portion of the aggregated patient data is displayed via a clinical case management tool 620, a viewer 622, and/or a hi-risk analysis tool 624, e.g. on the third party user devices 102, 104, 106.

In one or more implementations, the viewers 612, 622 and/or the high-risk analysis tools 614, 624 may include visual, graphical, statistical information displays of patient population trends that can be filtered by patient, by healthcare facility, by region, by state, by condition, or generally by any demographic or treatment grouping. The viewers 612, 622 and/or the high-risk analysis tools 614, 624 may display retrospective medical information, for patients that the third party organization is authorized to view, from the acute care setting and the outpatient setting regardless of the hospital. The trends may also be filtered based on time periods, such as daily, weekly, monthly, quarterly, annually, or generally any time period.

Figure 7:
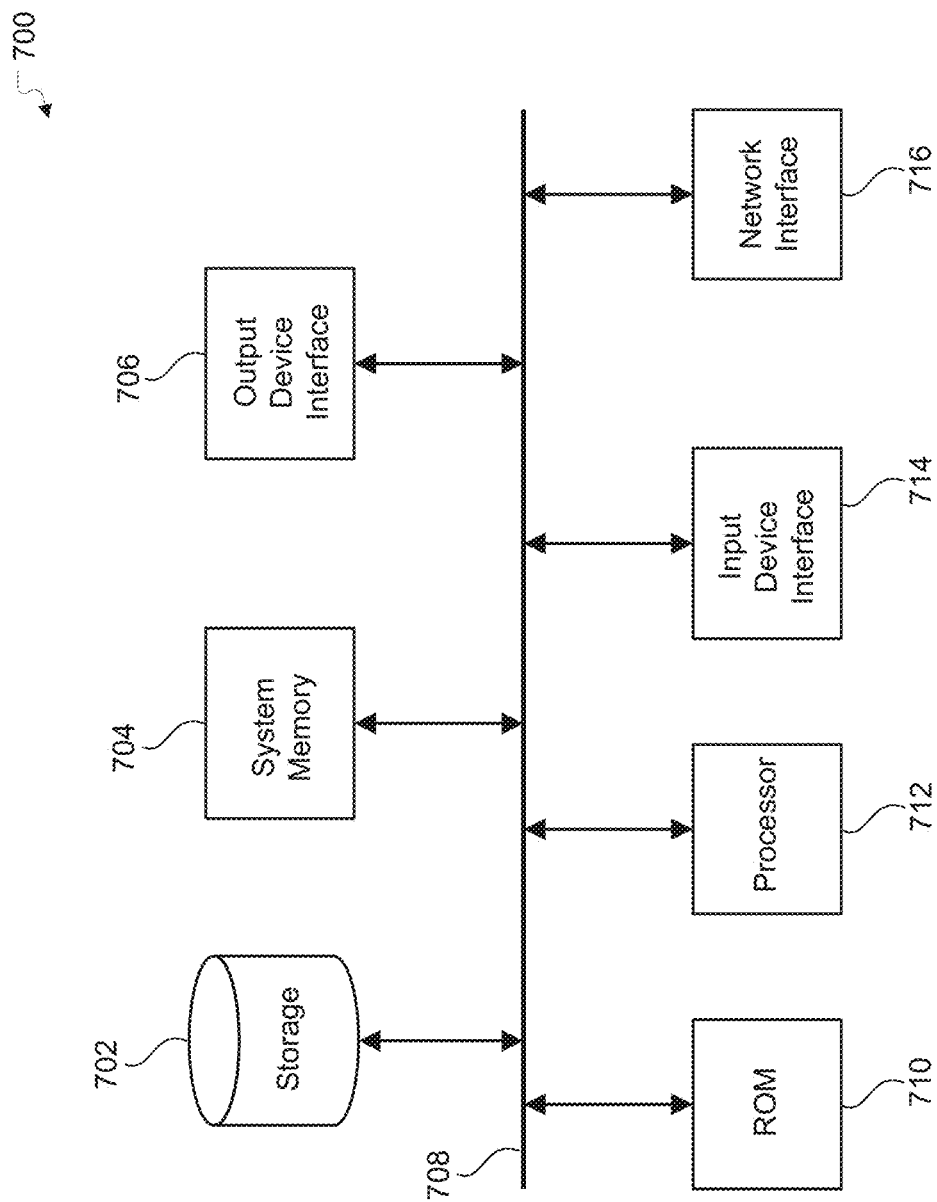
FIG. 7 conceptually illustrates an electronic system with which one or more implementations of the subject technology may be implemented.

FIG. 7 conceptually illustrates electronic system 700 with which one or more implementations of the subject technology may be implemented. Electronic system 700, for example, may be, or may be a part of, the patient data provider server 110, the third party servers 130A-C, the third party user devices 102, 104, 106, the interface system 225, the healthcare devices 210A-F, the healthcare data systems 220A-F, a desktop computer, a laptop computer, a tablet computer, a phone, a personal digital assistant (PDA), or generally any electronic device that transmits signals over a network. Such an electronic system includes various types of computer readable media and interfaces for various other types of computer readable media. Electronic system 700 includes bus 708, processing unit(s) 712, system memory 704, read-only memory (ROM) 710, permanent storage device 702, input device interface 714, output device interface 706, and network interface 716, or subsets and variations thereof.

Bus 708 collectively represents all system, peripheral, and chipset buses that communicatively connect the numerous internal devices of electronic system 700. In one or more implementations, bus 708 communicatively connects processing unit(s) 712 with ROM 710, system memory 704, and permanent storage device 702. From these various memory units, processing unit(s) 712 retrieves instructions to execute and data to process in order to execute the processes of the subject disclosure. The processing unit(s) can be a single processor or a multi-core processor in different implementations.

ROM 710 stores static data and instructions that are needed by processing unit(s) 712 and other modules of the electronic system. Permanent storage device 702, on the other hand, is a read-and-write memory device. This device is a non-volatile memory unit that stores instructions and data even when electronic system 700 is off. One or more implementations of the subject disclosure use a mass-storage device (such as a magnetic or optical disk and its corresponding disk drive) as permanent storage device 702.

Other implementations use a removable storage device (such as a floppy disk, flash drive, and its corresponding disk drive) as permanent storage device 702. Like permanent storage device 702, system memory 704 is a read-and-write memory device. However, unlike storage device 702, system memory 704 is a volatile read-and-write memory, such as random access memory. System memory 704 stores any of the instructions and data that processing unit(s) 712 needs at runtime. In one or more implementations, the processes of the subject disclosure are stored in system memory 704, permanent storage device 702, and/or ROM 710. From these various memory units, processing unit(s) 712 retrieves instructions to execute and data to process in order to execute the processes of one or more implementations.

Bus 708 also connects to input and output device interfaces 714 and 706. Input device interface 714 enables a user to communicate information and select commands to the electronic system. Input devices used with input device interface 714 include, for example, alphanumeric keyboards, pointing devices (also called "cursor control devices"), scanning devices, such as bar code scanners, RFID scanners, or generally any device that can receive input. Output device interface 706 enables, for example, the display of images generated by electronic system 700. Output devices used with output device interface 706 include, for example, printers and display devices, such as a liquid crystal display (LCD), a light emitting diode (LED) display, an organic light emitting diode (OLED) display, a flexible display, a flat panel display, a solid state display, a projector, or any other device for outputting information. One or more implementations may include devices that function as both input and output devices, such as a touch screen. In these implementations, feedback provided to the user can be any form of sensory feedback, such as visual feedback, auditory feedback, or tactile feedback; and input from the user can be received in any form, including acoustic, speech, or tactile input.

Finally, as shown in FIG. 7, bus 708 also couples electronic system 700 to a network (not shown) through network interface 716. In this manner, the computer can be a part of a network of computers (such as a local area network ("LAN"), a wide area network ("WAN"), or an Intranet, or a network of networks, such as the Internet. Any or all components of electronic system 700 can be used in conjunction with the subject disclosure.

Many of the above-described features and applications may be implemented as software processes that are specified as a set of instructions recorded on a computer readable storage medium (alternatively referred to as computer-readable media, machine-readable media, or machine-readable storage media). When these instructions are executed by one or more processing unit(s) (e.g., one or more processors, cores of processors, or other processing units), they cause the processing unit(s) to perform the actions indicated in the instructions. Examples of computer readable media include, but are not limited to, RAM, ROM, read-only compact discs (CD-ROM), recordable compact discs (CD-R), rewritable compact discs (CD-RW), read-only digital versatile discs (e.g., DVD-ROM, dual-layer DVD-ROM), a variety of recordable/rewritable DVDs (e.g., DVD-RAM, DVD-RW, DVD+RW, etc.), flash memory (e.g., SD cards, mini-SD cards, micro-SD cards, etc.), magnetic and/or solid state hard drives, ultra density optical discs, any other optical or magnetic media, and floppy disks. In one or more implementations, the computer readable media does not include carrier waves and electronic signals passing wirelessly or over wired connections, or any other ephemeral signals. For example, the computer readable media may be entirely restricted to tangible, physical objects that store information in a form that is readable by a computer. In one or more implementations, the computer readable media is non-transitory computer readable media, computer readable storage media, or non-transitory computer readable storage media.

In one or more implementations, a computer program product (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

While the above discussion primarily refers to microprocessor or multi-core processors that execute software, one or more implementations are performed by one or more integrated circuits, such as application specific integrated circuits (ASICs) or field programmable gate arrays (FPGAs). In one or more implementations, such integrated circuits execute instructions that are stored on the circuit itself.

Those of skill in the art would appreciate that the various illustrative blocks, modules, elements, components, methods, and algorithms described herein may be implemented as electronic hardware, computer software, or combinations of both. To illustrate this interchangeability of hardware and software, various illustrative blocks, modules, elements, components, methods, and algorithms have been described above generally in terms of their functionality. Whether such functionality is implemented as hardware or software depends upon the particular application and design constraints imposed on the overall system. Skilled artisans may implement the described functionality in varying ways for each particular application. Various components and blocks may be arranged differently (e.g., arranged in a different order, or partitioned in a different way) all without departing from the scope of the subject technology.

It is understood that any specific order or hierarchy of blocks in the processes disclosed is an illustration of example approaches. Based upon design preferences, it is understood that the specific order or hierarchy of blocks in the processes may be rearranged, or that all illustrated blocks be performed. Any of the blocks may be performed simultaneously. In one or more implementations, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products.

As used herein, the phrase "at least one of" preceding a series of items, with the term "and" or "or" to separate any of the items, modifies the list as a whole, rather than each member of the list (i.e., each item). The phrase "at least one of" does not require selection of at least one of each item listed; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The predicate words "configured to", "operable to", and "programmed to" do not imply any particular tangible or intangible modification of a subject, but, rather, are intended to be used interchangeably. In one or more implementations, a processor configured to monitor and control an operation or a component may also mean the processor being programmed to monitor and control the operation or the processor being operable to monitor and control the operation. Likewise, a processor configured to execute code can be construed as a processor programmed to execute code or operable to execute code.

A phrase such as "an aspect" does not imply that such aspect is essential to the subject technology or that such aspect applies to all configurations of the subject technology. A disclosure relating to an aspect may apply to all configurations, or one or more configurations. An aspect may provide one or more examples of the disclosure. A phrase such as an "aspect" may refer to one or more aspects and vice versa. A phrase such as an "embodiment" does not imply that such embodiment is essential to the subject technology or that such embodiment applies to all configurations of the subject technology. A disclosure relating to an embodiment may apply to all embodiments, or one or more embodiments. An embodiment may provide one or more examples of the disclosure. A phrase such an "embodiment" may refer to one or more embodiments and vice versa. A phrase such as a "configuration" does not imply that such configuration is essential to the subject technology or that such configuration applies to all configurations of the subject technology. A disclosure relating to a configuration may apply to all configurations, or one or more configurations. A configuration may provide one or more examples of the disclosure. A phrase such as a "configuration" may refer to one or more configurations and vice versa.

The word "exemplary" is used herein to mean "serving as an example, instance, or illustration." Any embodiment described herein as "exemplary" or as an "example" is not necessarily to be construed as preferred or advantageous over other embodiments. Furthermore, to the extent that the term "include," "have," or the like is used in the description or the claims, such term is intended to be inclusive in a manner similar to the term "comprise" as "comprise" is interpreted when employed as a transitional word in a claim.

All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The previous description is provided to enable any person skilled in the art to practice the various aspects described herein. Various modifications to these aspects will be readily apparent to those skilled in the art, and the generic principles defined herein may be applied to other aspects. Thus, the claims are not intended to be limited to the aspects shown herein, but are to be accorded the full scope consistent with the language claims, wherein reference to an element in the singular is not intended to mean "one and only one" unless specifically so stated, but rather "one or more." Unless specifically stated otherwise, the term "some" refers to one or more. Pronouns in the masculine (e.g., his) include the feminine and neuter gender (e.g., her and its) and vice versa. Headings and subheadings, if any, are used for convenience only and do not limit the subject disclosure.

What is claimed is:

1. A computer-implemented method, comprising:
providing an interface system in a healthcare organization, comprising a first adapter module interfacing the interface system with a healthcare data system and a second adapter module interfacing the interface system with a healthcare device within the healthcare organization, the healthcare device including an infusion device, ventilator, drug disposal device, or automated dispensing machine, and the healthcare data system including a pharmacy information system or a laboratory information system;
receiving, via the interface system, one or more first messages in a first message format of the healthcare data system from the healthcare data system via the first adapter module and one or more second messages in a second message format of the healthcare device from the healthcare device via the second adapter module, the one or more first messages comprising at least one clinical data item received from the healthcare data system and the one or more second messages comprising at least one healthcare device data item received from a respective healthcare device;

transforming the one or more first messages and the one or more second messages into an internal messaging format based on one or more predetermined transformation rules;

generating, in the internal messaging format of the interface system, from the transformed first and second messages, a plurality of patient data objects corresponding to a plurality of patients, each of the plurality of patient data objects comprising patient identifying information and being generated based on combining at least one clinical data item received from the healthcare data system and at least one healthcare device data item received from a respective healthcare device;

generating one or more first graphical user interfaces for a first third party organization and one or more second graphical user interfaces for a second third party organization, outside the healthcare organization;

providing, over a network by a server, the one or more first graphical user interfaces to one or more first devices associated with the first third party organization, and the one or more second graphical user interfaces to one or more second devices associated with the second third party organization;

receiving, via the one or more first graphical user interfaces, an user instruction to create a patient specific marker threshold for device information of the one or more second messages from the healthcare device, and to configure the server to designate a recipient in the first third party organization to receive notifications pertaining to the patient specific marker threshold;

creating the patient specific marker threshold responsive to the instruction and associating the patient specific marker threshold with the recipient in a database;

automatically determining, that one or more first patient data objects of the plurality of patient data includes a value of the device information that satisfies the patient specific marker threshold; and in response to the value of the one or more first patient data objects satisfying the patient specific marker threshold;

providing the determined one or more first patient data objects for display via the one or more first graphical user interfaces, wherein the first graphical user interfaces enables the recipient to filter respective patient data objects based on rules created by the recipient via the one or more first graphical user interfaces; and automatically causing a notification regarding the value to the recipient in the first third party organization pertaining to the provided one or more first patient data objects to be displayed via a dialog box or popup window in the one or more first graphical user interfaces.

2. The method of claim 1, further comprising:
generating a plurality of patient deidentified data objects based at least in part on an access privilege of the first third party organization and based on a first data transformation data rule associated with the first third party organization.

3. The method of claim 1, further comprising:
receiving at least one data function for the second third party organization, the at least one data function associated with identifying an outbreak of an illness;
applying the at least one data function to one or more of the plurality of patient data objects; and
identifying one or more patients associated with the illness based on the applying of the at least one data function.

4. The method of claim 1, further comprising:
determining a subset of the plurality of patients for which the first or second third party organization is authorized to view the corresponding subset of the plurality of patient data objects; and
generating a filtered plurality of patient data objects from the subset of the plurality of patient data objects when generating the plurality of patient data objects.

5. The method of claim 1, further comprising:
normalizing data within the plurality of patient data objects based at least in part on at least one data normalization rule associated with the first third party organization or the second third party organization, respectively.

6. The method of claim 1, wherein the healthcare device comprises a ventilator device, an infusion device, or an automated dispensing device.

7. The method of claim 1, wherein the healthcare data system comprises a laboratory information system.

8. The method of claim 1, further comprising:
generating trend information based at least in part on the plurality of patient data objects; and
providing, to at least one device associated with the first or second third party organization, a user interface for display that includes at least a portion of the trend information and a filter for filtering the trend information.

9. The method of claim 8, wherein the filter comprises a location filter that is configured to filter the trend information based on locations of the plurality of patients corresponding to filtered plurality of patient data objects.

10. The method of claim 8, wherein the filter comprises a condition filter that is configured to filter the trend information based on conditions associated with the plurality of patients corresponding to the filtered plurality of patient data objects, or the filter comprises a time filter that is configured to filter the trend information based on time periods associated with the filtered plurality of patient data objects.

11. A system, comprising:
one or more processors; and
one or more non-transitory machine readable memory devices storing instructions that, when executed by the one or more processors, cause the one or more processors to:
provide first and second adapter modules, a first adapter module interfacing an interface system with a healthcare device within a healthcare organization and a second adapter module interfacing the interface system with a healthcare data system, the healthcare device including an infusion device, ventilator, drug disposal device, or automated dispensing machine, and the healthcare data system including a pharmacy information system or a laboratory information system;
receive, in the interface system, from one or more of the first and second adapter modules, one or more first messages in a first message format of a healthcare data system from the healthcare data system via the first adapter module; and one or more second messages in a second message format of the healthcare device from the healthcare device via; from the a second adapter module, the one or more first messages comprising at least one clinical data item received from the healthcare data system and the one or more second messages comprising at least one healthcare device data item received from a respective healthcare device, in a second message format;

transform the one or more first messages and the one or more second messages into an internal messaging format based on one or more predetermined transformation rules;

generate, in the internal messaging format, from the transformed first and second messages, a plurality of patient data objects corresponding to a plurality of patients, each of the plurality of patient data objects comprising patient identifying information being generated based on combining and at least one clinical data item received from the healthcare data system and at least one healthcare device data item received from a respective healthcare device;

generate one or more first graphical user interfaces for a first third party organization and one or more second graphical user interfaces for a second third party organization, outside the healthcare organization;

provide, over a network, the one or more first graphical user interfaces to one or more first devices associated with the first third party organization, and the one or more second graphical user interfaces to one or more second devices associated with the second third party organization;

receiving, via the one or more first graphical user interfaces, an user instruction to create a patient specific marker threshold for device information of the one or more second messages from the healthcare device, and to configure a server to designate a recipient in the first third party organization to receive notifications pertaining to the patient specific marker threshold;

creating the patient specific marker threshold responsive to the instruction and associating the patient specific marker threshold with the recipient in a database;

automatically determining, that a value of a first patient data object of the plurality of patient data objects satisfies the patient specific marker threshold: and in response to the value of the first patient data object satisfying the patient specific marker threshold:

provide the determined one or more first patient data objects for display via the one or more first graphical user interfaces, wherein the first graphical user interfaces enables the recipient to filter respective patient data objects based on rules created by the recipient via the one or more first graphical user interfaces; and automatically send a notification regarding the value to the recipient in the first third party organization pertaining to the provided one or more first patient data objects to be displayed via a dialog box or popup window in the one or more first graphical user interfaces.

12. The system of claim 11, wherein the instructions further cause the one or more processors to:

generate a plurality of patient deidentified data objects based at least in part on an access privilege of the first third party organization.

13. The system of claim 11, wherein the instructions further cause the one or more processors to:

receive at least one data function associated with identifying an outbreak of an illness;

apply the at least one data function to one or more of the plurality of patient data objects; and identify one or more patients associated with the illness based on the applying of the at least one data function.

14. The system of claim 11, wherein the instructions further cause the one or more processors to:

determine a subset of the plurality of patients for which the first or second third party organization is authorized to view the corresponding subset of the plurality of patient data objects; and generate a filtered plurality of patient data objects from the subset of the plurality of patient data objects.

15. The system of claim 11, wherein the instructions further cause the one or more processors to:

normalize data within the first plurality of patient deidentified data objects or the second plurality of patient identifying data objects based at least in part on at least one data normalization rule associated with the first third party organization or the second third party organization, respectively.

16. The system of claim 11, wherein the healthcare device comprises an infusion device.

17. The system of claim 11, wherein the instructions further cause the one or more processors to:

generate trend information based at least in part on the plurality of patient data objects; and provide, to at least one device associated with the first or second third party organization, a user interface for display that includes at least a portion of the trend information and a filter for filtering the trend information.

18. The system of claim 17, wherein the filter comprises a location filter that is configured to filter the trend information based on locations of the plurality of patients corresponding to the filtered plurality of patient data objects.

19. The system of claim 17, wherein the filter comprises a condition filter that is configured to filter the trend information based on conditions associated with the plurality of patients, or the filter comprises a time filter that is configured to filter the trend information based on time periods associated with the filtered plurality of patient data objects.

20. A non-transitory machine-readable medium embodying instructions that, when executed by a machine, configure the machine to perform operations comprising:

providing an interface system in a healthcare organization, comprising a first adapter module interfacing the interface system with a healthcare data system and a second adapter module interfacing the interface system with a healthcare device within the healthcare organization, the healthcare device including an infusion device, ventilator, drug disposal device, or automated dispensing machine, and the healthcare data system including a pharmacy information system or a laboratory information system;

receiving, via the interface system, from the first and second adapter modules, one or more first messages in a first message format of the healthcare data system, and one or more second messages, in a second message format of the healthcare device, the one or more first messages comprising at least one clinical data item received from the healthcare data system and the one or more second messages comprising at least one healthcare device data item received from a respective healthcare device;

transforming the one or more first messages and the one or more second messages into an internal messaging format based on one or more predetermined transformation rules;

generating, in the internal messaging format of the interface system, from the transformed first and second messages, a plurality of patient data objects corresponding to a plurality of patients, each of the plurality of patient data objects comprising patient identifying information and being generated based on combining at least one clinical data item received from the healthcare data system and at least one healthcare device data item received from a respective healthcare device;

generating one or more first graphical user interfaces for a first third party organization and one or more second graphical user interfaces for a second third party organization, outside the healthcare organization;

providing, over a network, the one or more first graphical user interfaces to one or more first devices associated with the first third party organization, and the one or more second graphical user interfaces to one or more second devices associated with the second third party organization;

receiving, via the one or more first graphical user interfaces, an user instruction to create a patient specific marker threshold for device information of the one or more second messages from the healthcare device, and to configure a server to designate a recipient in the first third party organization to receive notifications pertaining to the patient specific marker threshold;

creating the patient specific marker threshold responsive to the instruction and associating the patient specific marker threshold with the recipient in a database;

automatically determining, that one or more first patient data objects of the plurality of patient data includes a value of the device information that satisfies the patient specific marker threshold; and in response to the value of the one or more first patient data objects satisfying the patient specific marker threshold:

providing the determined one or more first patient data objects for display via the one or more first graphical user interfaces, wherein the first graphical user interfaces enables the recipient to filter respective patient data objects based on rules created by the recipient via the one or more first graphical user interfaces; and automatically causing a notification regarding the value to the recipient in the first third party organization pertaining to the provided one or more first patient objects to be displayed via a dialog box or popup window in the one or more first graphical user interfaces.

\* \* \* \* \*